US012642520B2

(12) United States Patent
Gamso et al.

(10) Patent No.: US 12,642,520 B2
(45) Date of Patent: Jun. 2, 2026

(54) SUTURE PASSER AND METHODS OF TISSUE REPAIR

(71) Applicant: Arthrex, Inc., Naples, FL (US)

(72) Inventors: Nathanael I. Gamso, Bonita Springs, FL (US); Thomas Dooney, Jr., Naples, FL (US); Andrew C. Petry, Naples, FL (US); Shaun G. Leblanc, Naples, FL (US); Jennifer Brooks, Naples, FL (US)

(73) Assignee: ARTHREX, INC., Naples, FL (US)

( * ) Notice: Subject to any disclaimer, the term of this patent is extended or adjusted under 35 U.S.C. 154(b) by 363 days.

(21) Appl. No.: 18/090,593

(22) Filed: Dec. 29, 2022

(65) Prior Publication Data

US 2024/0215973 A1     Jul. 4, 2024

(51) Int. Cl.
*A61B 17/04*         (2006.01)
(52) U.S. Cl.
CPC .... *A61B 17/0469* (2013.01); *A61B 2017/047* (2013.01); *A61B 2017/0477* (2013.01)
(58) Field of Classification Search
CPC ............ A61B 17/0469; A61B 17/0482; A61B 17/0485; A61B 17/0483; A61B 2017/0477; A61B 2017/047
See application file for complete search history.

(56) References Cited

U.S. PATENT DOCUMENTS

| | | | | | |
|---|---|---|---|---|---|
| 1,822,330 | A | * | 9/1931 | Ainslie | A61B 17/0469 |
| | | | | | 606/145 |
| 5,312,423 | A | * | 5/1994 | Rosenbluth | A61B 17/12013 |
| | | | | | 606/139 |

| | | | | | |
|---|---|---|---|---|---|
| 5,643,293 | A | * | 7/1997 | Kogasaka | A61B 17/0469 |
| | | | | | 606/139 |
| 5,895,393 | A | * | 4/1999 | Pagedas | A61B 17/0483 |
| | | | | | 606/139 |
| 5,895,395 | A | * | 4/1999 | Yeung | A61B 17/0469 |
| | | | | | 606/139 |

(Continued)

FOREIGN PATENT DOCUMENTS

| | | |
|---|---|---|
| EP | 1306056 B1 | 5/2003 |
| EP | 2042104 A1 | 4/2009 |

(Continued)

OTHER PUBLICATIONS

International Search Report and Written Opinion for International Application No. PCT/US2023/082661 dated Jun. 28, 2024.

(Continued)

*Primary Examiner* — Alexander J Orkin

(74) *Attorney, Agent, or Firm* — Potomac Law Group, PLLC

(57)     ABSTRACT

Methods for tissue repairs with mattress stitch are disclosed. A mattress stitch is created with a suture passer and a suturing construct using only one portal and without shuttling steps. The suture passer is provided with two sharp teeth or tines that pierce tissue (or tissue and associated graft) at two different locations. The suturing construct can be a loop terminating in a tail. The tail is passed from one tooth to another and then secured into a securing mechanism of one of the two sharp teeth. The tail is passed through the loop to form a cinch loop around and through the tissue (or the tissue and the graft).

8 Claims, 8 Drawing Sheets

(56)                    References Cited

U.S. PATENT DOCUMENTS

| | | | | |
|---|---|---|---|---|
| 8,177,795 | B2 * | 5/2012 | Niese | A61B 17/0482 |
| | | | | 606/144 |
| 9,358,001 | B2 | 6/2016 | Fan et al. | |
| 10,004,489 | B2 | 6/2018 | Kaiser et al. | |
| 10,022,122 | B2 | 7/2018 | Singhatat et al. | |
| 11,013,510 | B2 | 5/2021 | Saliman et al. | |
| 11,389,156 | B2 | 7/2022 | Harrison et al. | |
| 12,082,801 | B2 | 9/2024 | Dooney, Jr. et al. | |
| 12,096,928 | B2 | 9/2024 | Kaiser et al. | |
| 2002/0103493 | A1 * | 8/2002 | Thal | A61B 17/0469 |
| | | | | 606/144 |
| 2003/0078599 | A1 | 4/2003 | O'Quinn et al. | |
| 2004/0260314 | A1 * | 12/2004 | Lizardi | A61B 17/0469 |
| | | | | 606/144 |
| 2007/0225735 | A1 * | 9/2007 | Stone | A61B 17/0625 |
| | | | | 606/144 |
| 2007/0276395 | A1 * | 11/2007 | Burn | A61B 17/0483 |
| | | | | 606/80 |
| 2008/0027468 | A1 * | 1/2008 | Fenton, Jr. | A61B 17/062 |
| | | | | 606/222 |
| 2008/0154286 | A1 * | 6/2008 | Abbott | A61B 17/0483 |
| | | | | 606/228 |
| 2008/0208221 | A1 * | 8/2008 | Murray | A61B 17/0625 |
| | | | | 606/145 |
| 2009/0088781 | A1 * | 4/2009 | Prestel | A61B 17/0469 |
| | | | | 606/148 |
| 2009/0228041 | A1 * | 9/2009 | Domingo | A61B 17/06066 |
| | | | | 606/144 |
| 2010/0106169 | A1 | 4/2010 | Niese et al. | |
| 2010/0305581 | A1 * | 12/2010 | Hart | A61B 17/0625 |
| | | | | 606/139 |
| 2012/0283753 | A1 * | 11/2012 | Saliman | A61B 17/0482 |
| | | | | 606/145 |
| 2012/0283754 | A1 * | 11/2012 | Murillo | A61B 17/0469 |
| | | | | 606/145 |
| 2013/0158567 | A1 | 6/2013 | Levin et al. | |
| 2014/0052178 | A1 | 2/2014 | Dooney, Jr. | |
| 2014/0249577 | A1 | 9/2014 | Pilgeram | |
| 2014/0277133 | A1 | 9/2014 | Foerster | |
| 2015/0173739 | A1 | 6/2015 | Rodriguez et al. | |
| 2015/0173742 | A1 | 6/2015 | Palese et al. | |
| 2016/0157904 | A1 * | 6/2016 | Zeetser | A61B 17/842 |
| | | | | 606/280 |
| 2017/0049432 | A1 | 2/2017 | Dooney, Jr. et al. | |
| 2017/0112492 | A1 * | 4/2017 | Juan | A61B 17/0487 |
| 2018/0125472 | A1 | 5/2018 | Dreyfuss | |
| 2019/0247039 | A1 | 8/2019 | Gregoire et al. | |
| 2020/0054439 | A1 | 2/2020 | Holowecky et al. | |
| 2020/0138429 | A1 | 5/2020 | Dreyfuss et al. | |
| 2020/0275922 | A1 | 9/2020 | Valentin et al. | |
| 2021/0236115 | A1 * | 8/2021 | Radfar | A61B 17/0469 |
| 2021/0275165 | A1 * | 9/2021 | Rash | A61B 17/0469 |

FOREIGN PATENT DOCUMENTS

| | | |
|---|---|---|
| WO | 2009111591 A2 | 9/2009 |
| WO | 2013093620 A2 | 6/2013 |

OTHER PUBLICATIONS

Invitation to Pay Additional Fees For International Application No. PCT/US2023/082661 dated Apr. 15, 2023.

International Search Report and Written Opinion for International Application No. PCT/US2024/023656 dated Sep. 27, 2024.

Invitation to pay Additional Fees for International Application No. PCT/US2024/023656 dated Jul. 15, 2024.

Unknown. " The Cross Fix II System," Zimmer Biomet, health care professional material, 2018.

Extended European Search Report issued in EP Pat. Appln. No. 23913433.1 and dated Mar. 19, 2026.

* cited by examiner

SUTURE PASSER AND METHODS OF TISSUE REPAIR

BACKGROUND

The disclosure relates to the field of surgery and, more specifically, to instruments and methods of passing suture.

SUMMARY

Instruments and methods for surgical repairs are disclosed. A suture passer is provided with means to penetrate two distinct points in a tissue and blindly pass and retrieve suture through an area of the tissue. Means can include sharp teeth and/or pointed structures.

Methods of passing suture are also disclosed. A flexible strand can be passed blindly through tissue with a suture passer. A flexible strand can be blindly passed horizontally underneath tissue. Teeth of the suture passer can pierce through tissue at desired locations of entry and exit of the flexible strand. A needle can pass from one tooth to the other, passing a flexible strand from one tooth to the other tooth and up through the tissue.

DETAILED DESCRIPTION

Figure 1:
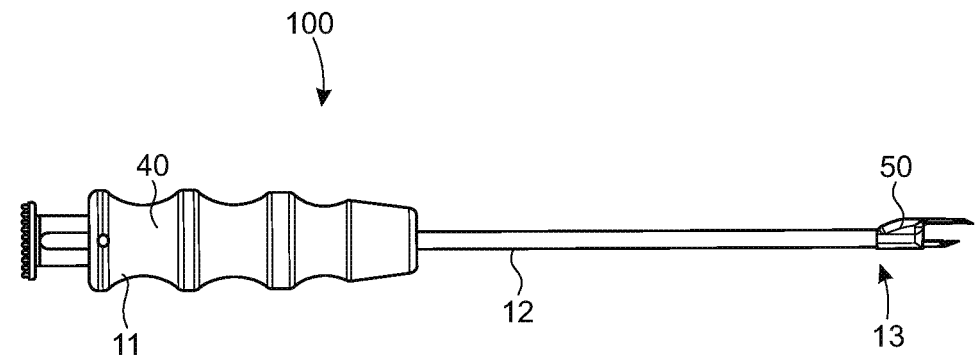
FIG. 1 illustrates a suture passing instrument.

The disclosure provides surgical systems, assemblies, constructs, and methods for tissue repairs and reconstructions.

A suture passing instrument is provided with means to penetrate two distinct points in a tissue (or tissue and associated graft) and blindly pass and retrieve suture through an area of the tissue. Means can include sharp teeth and/or pointed structures such as tines.

Methods of passing suture are also disclosed. A flexible strand can be passed blindly through tissue (or tissue and associated graft) with a suture passer. A flexible strand can be blindly passed horizontally underneath tissue (or tissue and graft). Teeth of the suture passer can pierce through tissue (or tissue and graft) at desired locations of entry and exit of the flexible strand. A needle can pass from one tooth to the other, passing a flexible strand to the other tooth and up through the tissue (or tissue and graft).

In an embodiment, the suture passing instrument is employed for shoulder repairs such as a shoulder mattress repair. The repair can include a cerclage loop. The repair can include a Weston loop. The repair can include one or more knots. The repair can be a knotless repair. The repair can be a knotted repair. The repair can be a soft tissue repair, such as tendon, ligament, muscle, etc., repair. The repair can secure graft to tissue. The repair can secure tissue to tissue.

Techniques for surgical repairs such as endoscopic surgical repairs (for example, arthroscopic surgeries) are also disclosed. A first portion of a flexible construct is passed through two separate points or locations in tissue (or tissue and associated graft), the suture passer is removed, and the first portion of the flexible construct is passed through a second portion of the same flexible construct to form a stitch. The second portion of the flexible construct can be a pre-formed loop. The flexible construct can be a suture loop terminating in a single tail. In an embodiment, the tissue can be soft tissue such as tendon or ligament. In an embodiment, the tissue can be a capsule. In an embodiment, the repair can be conducted on tissue and graft overlying the tissue. A suture passer can facilitate suture placement in soft tissue (or soft tissue and graft) and formation of a mattress stitch through a single arthroscopic portal and without shuttling steps.

A suture passing instrument can include an elongated tubular member that has a channel and a distal tip configured to penetrate and pierce tissue. The distal tip can include two sharp teeth or tines. The teeth or tines can have different dimensions. The teeth or tines can have different lengths. The teeth or tines can penetrate tissue (or tissue and graft) at about the same time and at two different locations. The suture passing instrument is loaded with a flexible construct in the form of a pre-formed suture loop terminating in a single tail. The suture passing instrument can include a handle assembly located at the proximal end of the elongated tubular member. The tip is located at the distal end of the elongated tubular member. The handle assembly can house a mechanism for facilitating advancing and retracting of a needle and flexible construct.

In an embodiment, a suture passer comprises: a hollow shaft having a longitudinal axis, a distal end, and a proximal end; a tip at the distal end of the shaft, the tip having two sharp teeth of different lengths, each of the sharp teeth having an opening for a flexible construct to pass through and a pointed end for penetrating tissue or tissue and graft (for example, piercing through tissue, or through tissue and graft); and a flexible construct in the form of a loop with one or more tails, wherein one of the tails is secured to one of the teeth. The tail of the flexible construct is configured to be passed from one tooth to the other tooth, to exit the tissue, and to pass through the loop of the flexible construct. In an embodiment, the loop is a pre-formed loop secured to the shaft of the suture passer instrument. The pre-formed loop can terminate in one or more tails. In an embodiment, the loop is a continuous, flexible uninterrupted loop that terminates in a single tail.

Methods of suturing tissue are also disclosed. In an embodiment, tissue can be sutured by securing a tail of a flexible strand to a tine of a suture passing instrument; passing the suture passing instrument through tissue (or tissue and graft) so that the suture passing instrument pierces the tissue (or tissue and graft) at two different locations; subsequently, advancing a needle to allow the tail to pass through tissue (or tissue and graft) from a first location to a second location; removing the suture passing instrument to allow the tail to exit the tissue (or tissue and graft); and passing the tail through a loop of the flexible strand to form a cinch (a continuous, uninterrupted loop of the flexible strand) through and around the tissue. The steps can be repeated to form a mattress stitch.

An exemplary method of suturing tissue comprises: (i) securing a flexible construct formed of a flexible strand with a loop terminating in a single tail to a suture passer; (ii) piercing tissue (or tissue and graft) with the suture passer at two different locations within the tissue (or tissue and graft); (iii) advancing the tail of the flexible construct from one region of the tip to another region of the tip and pulling the suture passer out of the tissue (or tissue and graft); (iv) passing the single tail through the loop of the flexible construct to form a suture pass cinch loop; and (v) pulling the single tail to complete the tension on the cinch loop. The method can be conducted through a single portal and without additional shuttling steps and instrumentation.

Referring now to the drawings, where like elements are designated by like reference numerals, FIGS. 1-23 illustrate suture passing instrument 100 and flexible construct 80 employed in exemplary methods of tissue repairs 101, 102 (shoulder repairs 101, 102) of the present disclosure.

Figure 2:
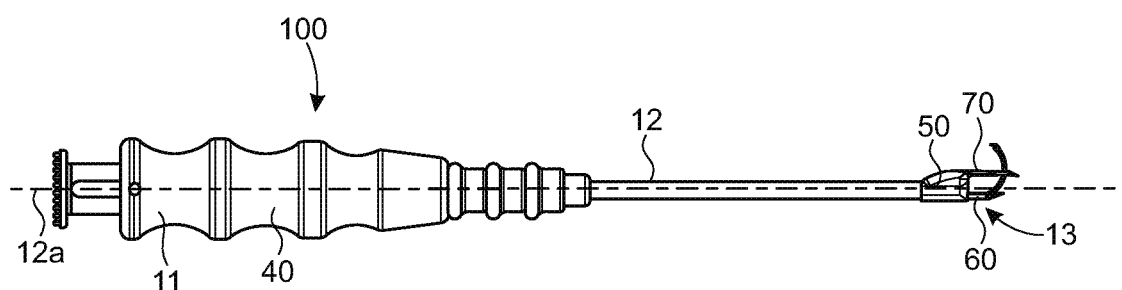
FIG. 2 illustrates a side view of the suture passing instrument of FIG. 1 (with the needle advanced).

As shown in FIGS. 1 and 2, suture passing instrument 100 (suture passer 100; instrument 100; surgical instrument 100; assembly 100) comprises an elongated tubular member or shaft 12 having a longitudinal axis 12a, a proximal end 11, a distal end 13 and an axial throughbore therein. Shaft 12 may be a tube or a narrow-diameter rod of dimensions that permit the tubular member to be introduced through an associated cannula (for example, an 8.25 cannula) in a minimally invasive procedure, such as arthroscopic or other endoscopic procedures, or into a body cavity, such as the abdominal cavity.

Elongated tubular member 12 connects, and extends between, a handle assembly 40 and a tip 50 designed to pierce tissue (or tissue and associated graft). Tip 50 (illustrated enlarged in FIG. 3) is provided with first and second teeth 60, 70 (first and second jaws 60, 70; lower and upper jaws 60, 70; tines 60, 70; first and second jaw members 60, 70) provided integral with shaft 12. In an embodiment, first tooth 60 is a lower jaw provided with a sharp distal point 61, a passage 66 (not shown) for receiving a needle 30, and a distal opening 65 to allow the needle to pass through. Opening 65 also allows a first portion of flexible construct 80 (flexible strand 80) to pass and extend therethrough, as detailed below. Opening 65 is provided in a most distal end of tip 50 and communicates with the needle passage 66. Distal opening 65 allows suture 80 to be positioned within it in a direction non-parallel to the longitudinal axis of the instrument. In an embodiment, suture 80 can be positioned within opening 65 to rest about perpendicular to the longitudinal axis of the instrument.

In an embodiment, second tooth 70 is an upper jaw provided with a sharp distal point 71, and a distal opening 75 (window 75) to allow the needle 30 and flexible construct 80 to pass through. Opening/window 75 can be a through opening that allows a first portion of flexible construct 80 to pass and extend therethrough, as detailed below. Second tooth 70 also comprises a securing mechanism 77 (illustrated in more detail in FIG. 7) located in about same plane as the distal opening/window 75, to allow the first portion 81 of flexible construct 80 to be secured thereto when the device 100 is pulled out of the tissue (or tissue and associated graft).

Figure 3:
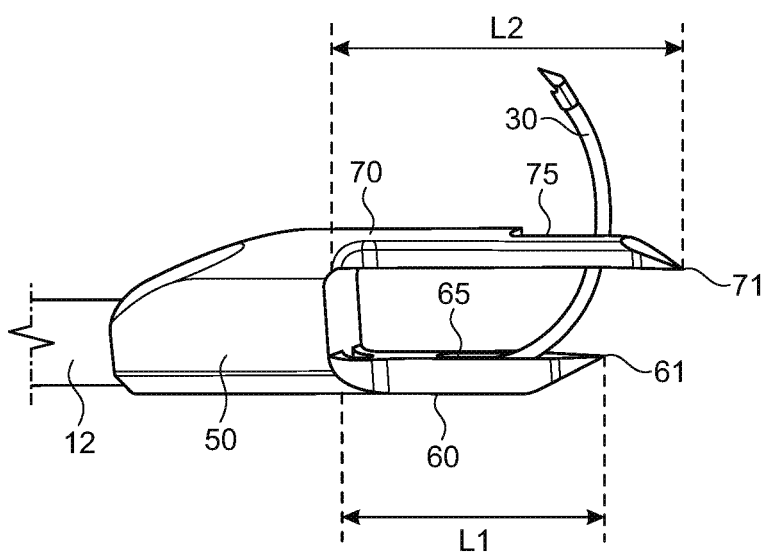
FIG. 3 illustrates an enlarged view of the tip of the suture passing instrument of FIG. 2.

In an embodiment, first tooth 60 has a length L1 which is different form a length L2 of the second tooth 70. In an embodiment, length L1 can be smaller than length L2, as shown in FIG. 3. Additional details and various views of tip 50 of instrument 100 are shown in FIGS. 20-23.

Flexible construct 80 is provided with a first portion 81 terminating with a second portion 85 in the form of a continuous, flexible uninterrupted loop 85. In an exemplary embodiment, flexible construct 80 is a FiberStick™ Link 80 provided with a first portion 81 which forms tail 81. Tail 81 can be stiffened to allow convenient and easy advancement through the tissue and openings 65, 75 of the suture passer 100. The second portion 85 can be in the form of a loop, for example, a continuous, flexible uninterrupted loop 85 terminating in the single tail 81.

Figure 4:
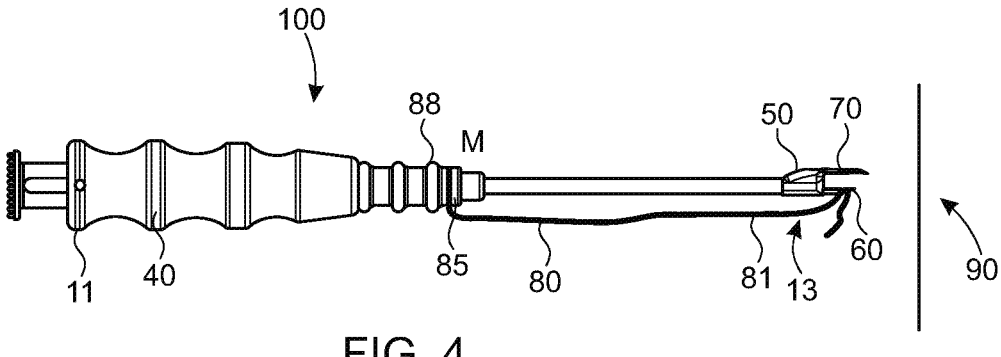
FIGS. 4-18 illustrate schematic subsequent steps of tissue repairs with the suture passing instrument of FIG. 1.
Figure 5:
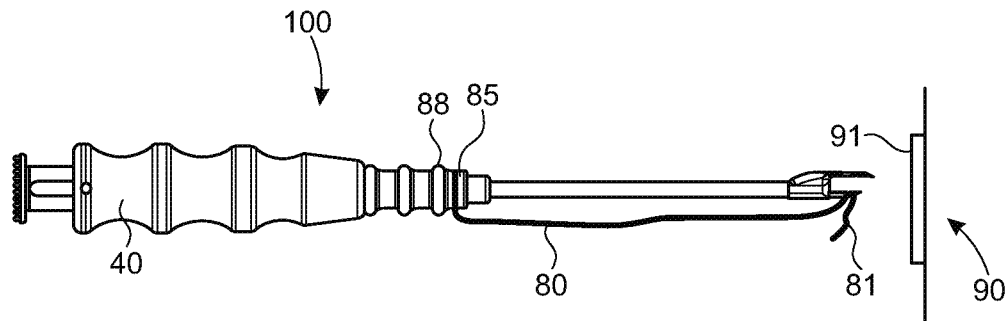
Figure 6:
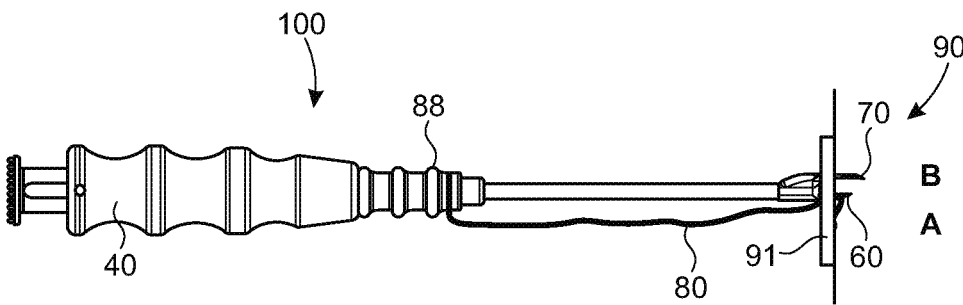
Figure 7:
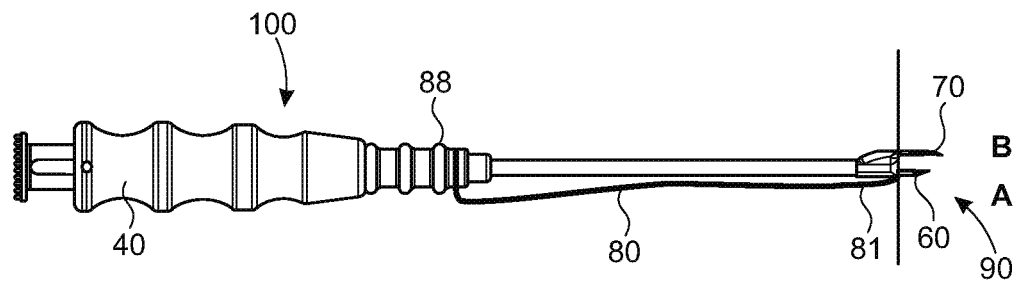

Reference is now made to FIGS. 4-18. Flexible strand 80 is loaded onto instrument 100 as shown in FIG. 4. Single tail 81 is loaded onto the lower jaw 60 (short tine 60) of suture passer 100. Loop 85 can be secured at about the middle of the instrument, i.e., at a point M located at about the middle distance between the proximal end 11 and the distal end 13 of the instrument 100.

Figure 17:
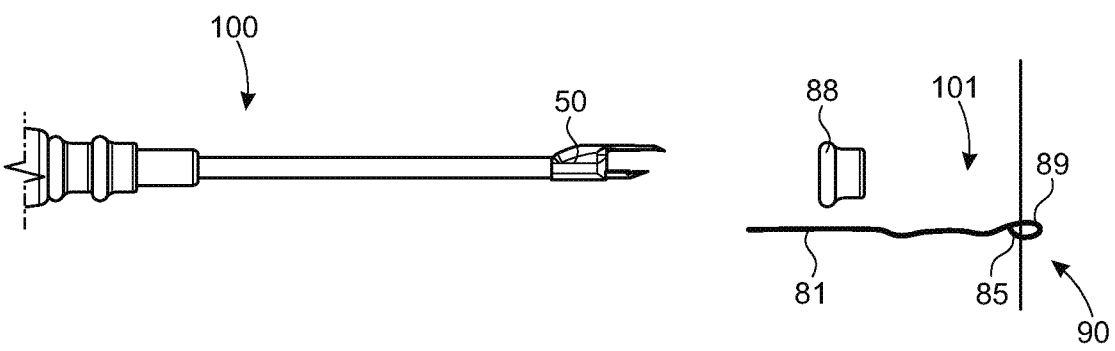
Figure 18:
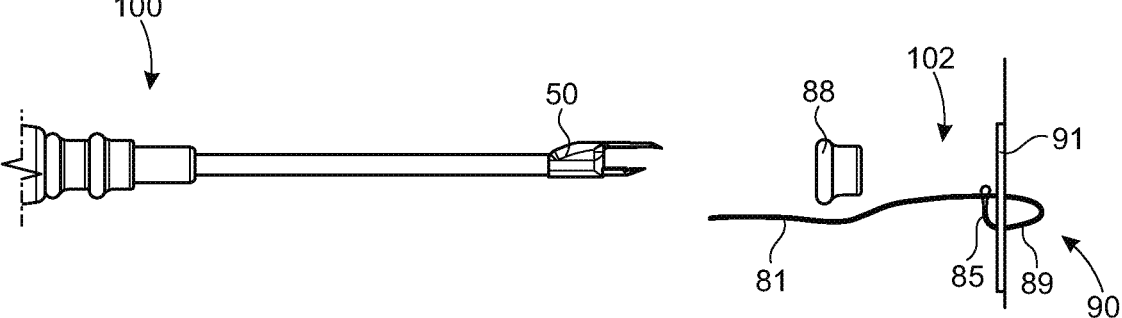
Figure 19:
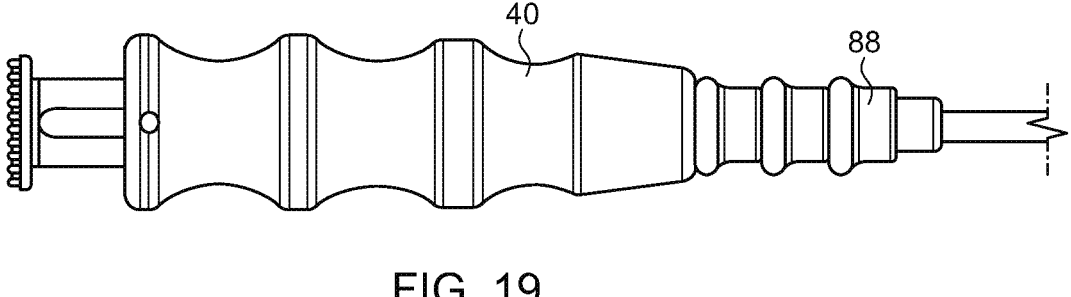
FIG. 19 illustrates an enlarged view of the tip of the suture passing instrument of FIG. 2.
Figure 20:
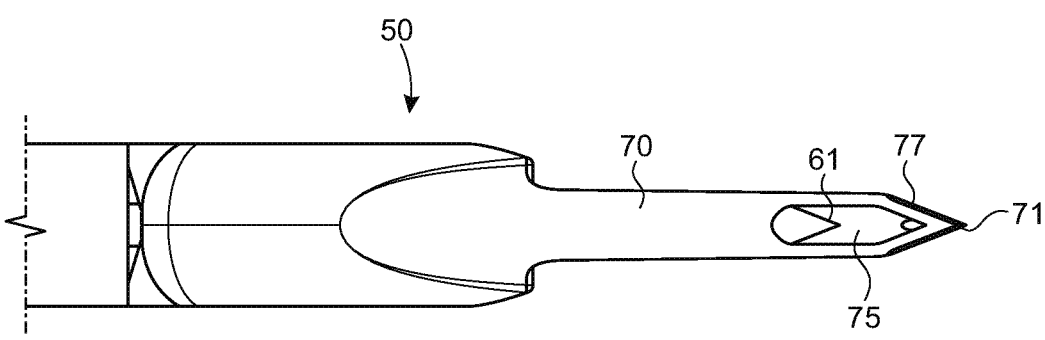
FIG. 20 illustrates an enlarged top view of the tip of the suture passing instrument of FIG. 1.
Figure 21:
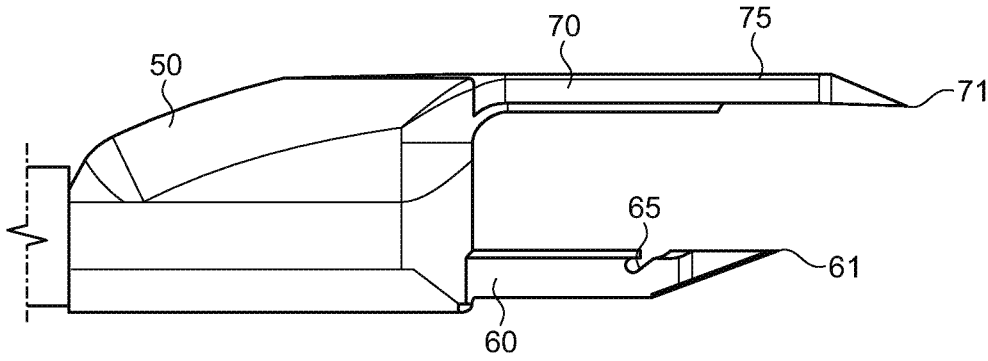
FIG. 21 illustrates an enlarged side view of the tip of the suture passing instrument of FIG. 1.
Figure 22:
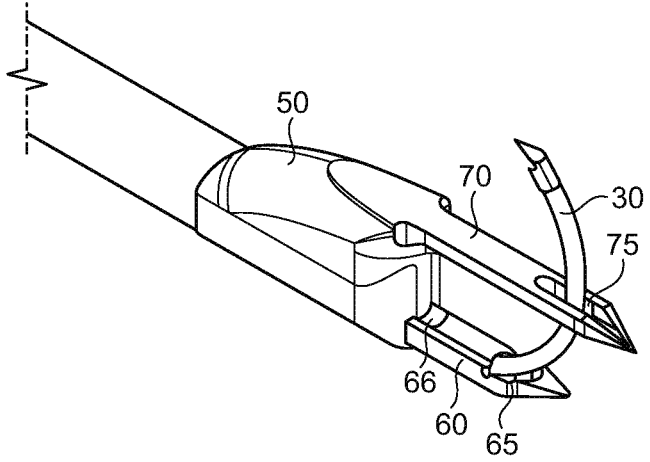
FIG. 22 illustrates an enlarged perspective view of the tip of the suture passing instrument of FIG. 2.
Figure 23:
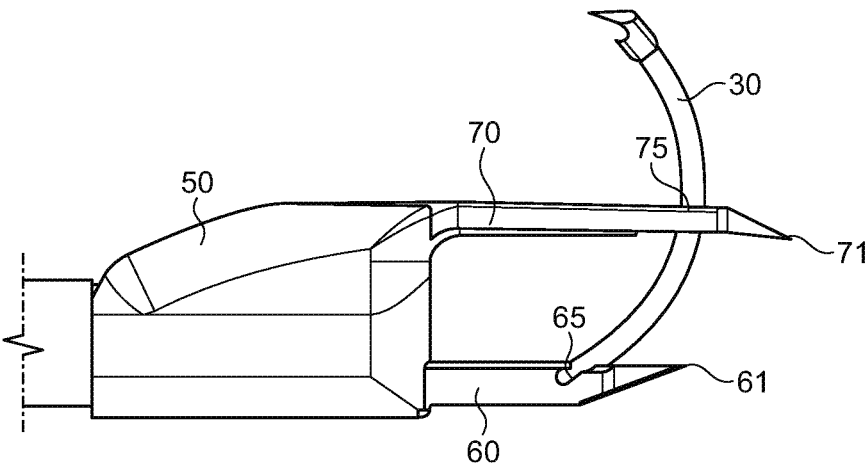
FIG. 23 illustrates an enlarged side view of the tip of the suture passing instrument of FIG. 2.

FIGS. 4-18 illustrate schematic steps of methods of tissue repairs (e.g., tendon or ligament repair, or attachment of graft to tissue) with instrument 100 loaded with exemplary flexible strand 80 (suturing construct 80; flexible construct 80; suture 80; flexible material 80). FIG. 17 illustrates exemplary repair 101 of soft tissue 90. FIG. 18 illustrates exemplary repair 102 for attaching graft 91 to soft tissue 90.

FIGS. 4-7: Instrument 100 loaded with flexible strand 80 is passed through tissue 90 (FIG. 7) or through tissue 90 and associated graft 91 (FIG. 6); instrument 100 pokes tissue 90 (or graft 91 and tissue 90), for example, pierces tissue 90 (or graft 91 and tissue 90) at two different locations A, B. Alternatively, instrument 100 can pass under the tissue 90 (e.g., tendon). Suture 80 is loaded onto the short tine 60 of device 100. Suture 80 can be housed on a ring 88 towards the center M of the device containing a preformed loop 85 (cerclage 85) or a modified Weston loop 85. The distal end of instrument 100 is inserted through a cannula and into tissue 90 (or into tissue 90 and associated graft 91). The device 100 can be used in an open technique or an arthroscopic technique.

Figure 8:
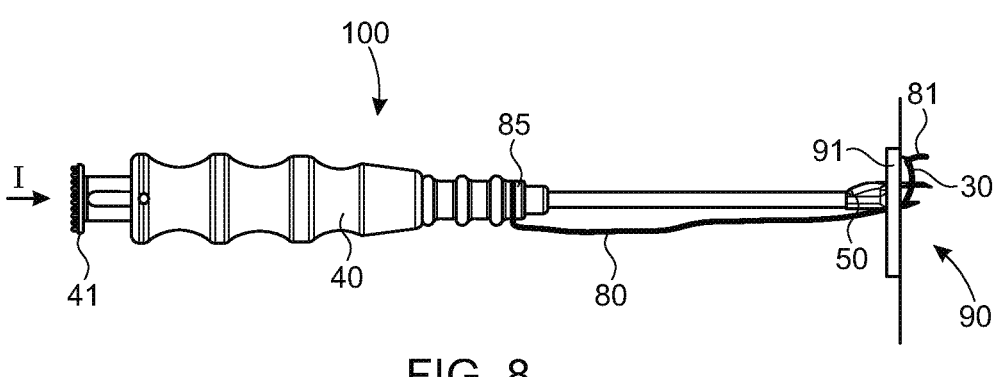
Figure 9:
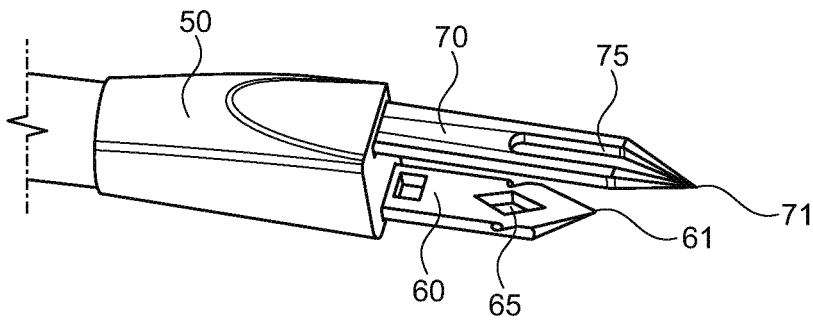

FIG. 8: Once the appropriate depth is attained in tissue 90 and associated graft 91, needle 30 is fired, transferring suture 81 through the opening/window 75 of the longer tine 70. Needle 30 can be advanced by pushing knob 41 of handle 40 in the direction of arrow I. FIG. 9 illustrates an enlarged view of the tip 50 of instrument 100.

Figure 10:
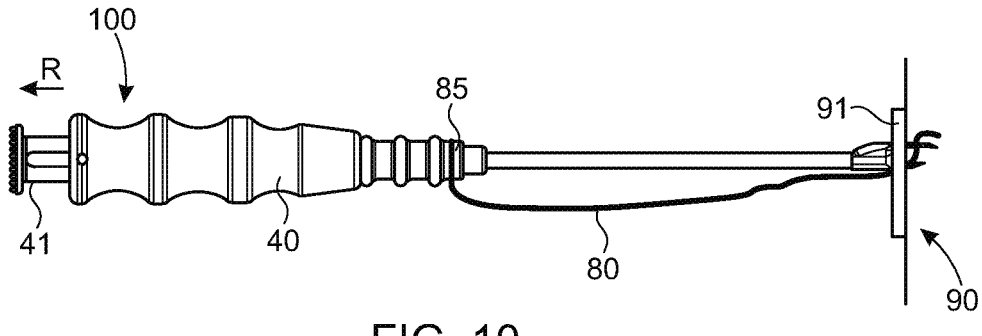

FIG. 10: The needle 30 is retracted back into the short tine 60 (by pulling the knob 41 of handle 40 in the direction of arrow R) leaving the suture 81 in the longer tine window.

Figure 11:
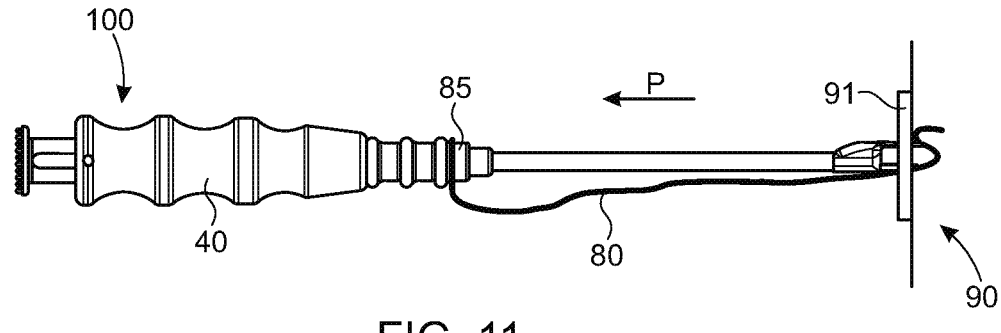
Figure 12:
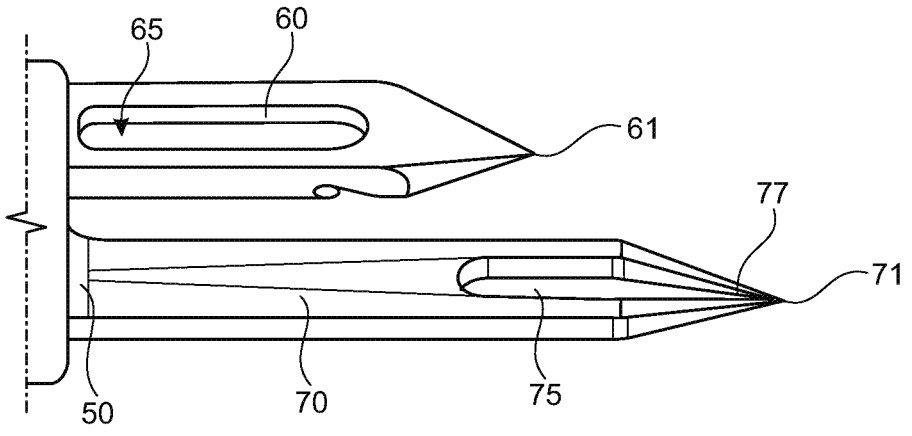

FIG. 11: The device 100 is pulled out of the tissue 90 and graft 91 in the direction of arrow P. The suture 81 folds over the distal wall of the longer tine opening/window 75 and catches on a suture catch spike 77 (securing mechanism 77). FIG. 12 illustrates an enlarged view of the suture securing mechanism 77 of the upper tooth 70.

Figure 13:
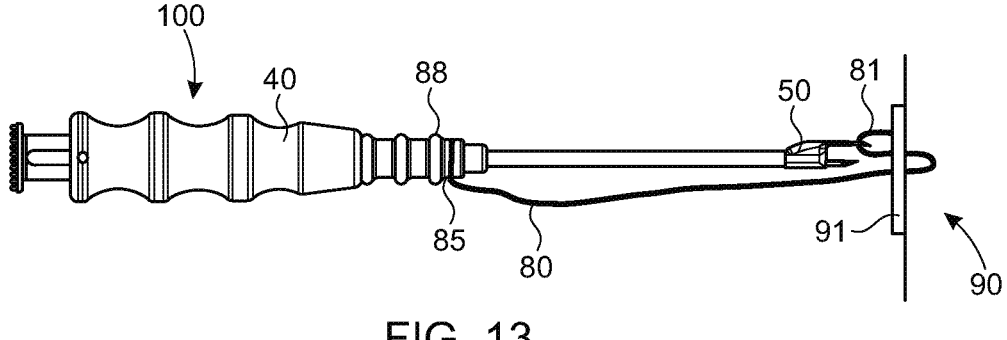

FIG. 13: The device 100 is pulled out of the cannula.

Figure 14:
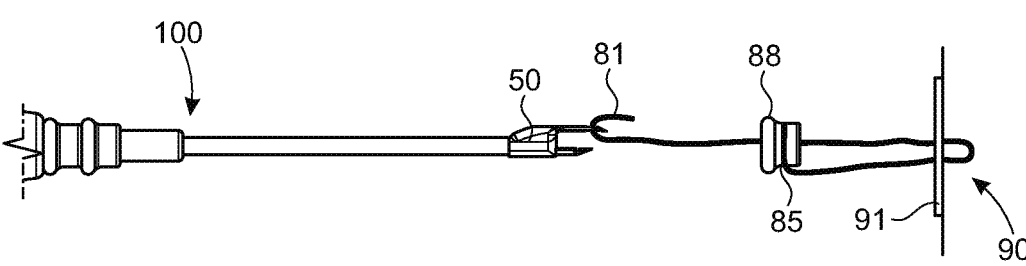

FIG. 14: The suture ring 88 is detached from the device 100 and slid over the distal end 13 of the device 100. With the suture 81 still attached to the longer tine 70 (at securing mechanism 77), the ring 88 is slid over the retained suture 81, thus converting the cerclage 85 or modified Weston loop 85 to a suture cinch 89.

Figure 15:
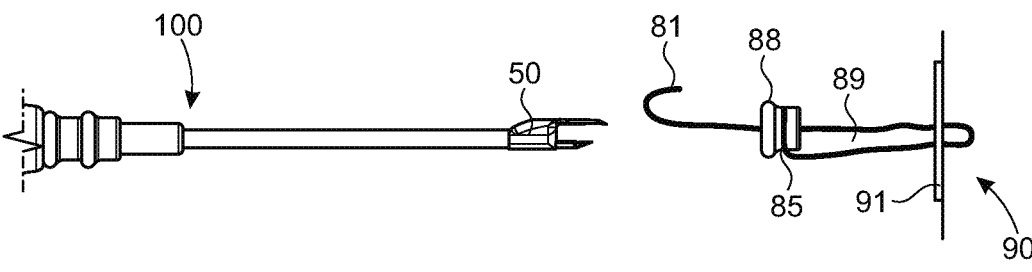

FIG. 15: Suture 81 is released from the longer tine 70.

Figure 16:
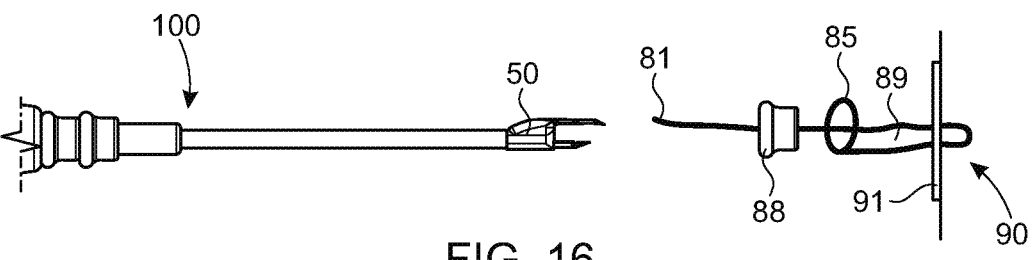

FIG. 16: The pre-formed loop 85 (cerclage loop 85) or modified Weston loop 85 is removed from the ring 88, as shown.

FIG. 17: The ring 88 is removed and cinch loop 89 is tensioned until adequate tension is created at repair 101. The suture ring 88 can be discarded.

FIG. 18: The ring 88 is removed and cinch loop 89 is tensioned until adequate tension is created at repair 102. The suture ring 88 can be discarded.

Flexible strand 80 (suturing construct 80; flexible construct 80; suture 80; flexible material 80) can be formed of a single strand of material that is looped/joined to form loop 85 and single tail 81. In an embodiment, flexible strand 80 has a length and two ends that form a loop 85 terminating in a single tail 81. In an embodiment, flexible strand 80 has one end that forms loop 85 and the other end forming single tail 81 (flexible end 81). Loop 85 may be a continuous, uninterrupted, flexible loop formed of a material such as suture. Loop 85 can terminate in single flexible end or tail 81. In one embodiment, the perimeter of loop 85 may be fixed. In one embodiment, loop 85 and tail 81 may be formed of suture having a round cross-section. The suture may have the same or different diameters. Loop 85 may be formed by splicing the flexible strand through itself, or by other methods known in the art, such as fusion, gluing, bonding, joining, braiding, interlinking, etc.

Although the embodiments detailed above have been described with reference to the flexible strand 80 forming a continuous, uninterrupted, flexible loop 85 around ring 88, it must be understood that the disclosure is not limited to this exemplary-only embodiment; thus, the disclosure also contemplates a flexible strand that can form any loop, for example, a knotted loop or any similar structure, around any part of the instrument 100. In addition, flexible strand 80 can also include two terminal ends or tails in addition to one loop, so that the loop can be located in between and adjacent the two terminal ends/tails.

Flexible strand 80 can include a single filament, or fiber, or can include multiple continuous filaments, segments or regions of filaments that have different configurations (for example, different diameters and/or different compositions). The filament regions/segments may each be homogenous (i.e., formed of a same material) or may be a combination of homogenous and heterogenous (i.e., formed of a plurality of materials). Exemplary materials may include suture, silk, cotton, nylon, polypropylene, polyethylene, ultrahigh molecular weight polyethylene (UHMWPE), polyethylene terephthalate (PET), and polyesters and copolymers thereof, or combinations thereof.

In an embodiment, the flexible strand 80 is made of any known suture construct, such as multifilament, braided, knitted, woven suture, or including fibers of ultrahigh molecular weight polyethylene (UHMWPE) or the Fiber-Wire® suture (disclosed in U.S. Pat. No. 6,716,234, the disclosure of which is hereby incorporated by reference in its entirety herein). The flexible strand 80 can be also formed of suture tape, for example, Arthrex FiberTape®, which is a high strength suture tape that is braided and rectangular-like in cross section and as disclosed in U.S. Pat. No. 7,892,256, the disclosure of which is incorporated by reference in its entirety herein.

Flexible strand 80 can also include, and be manufactured with, any kind of material (suture, nylon, silk, UHMWPE. metal, bioabsorbable, etc.) that can allow the flexible strand to form a loop terminating in a single tail.

Instrument 100 and construct 80 can be employed in endoscopic surgery. The term "endoscopic surgery" refers to surgical procedures within a patient's body through small openings as opposed to conventional open surgery through large incisions.

According to an exemplary and illustrative embodiment only, a suture passer 100 comprises a shaft 12 having a longitudinal axis 12a, a distal end 13 and a proximal end 11;

a first jaw member 60 integral to the distal end 13 of the shaft 12, the first jaw member 60 having a passage 66 for receiving a needle 30 and a distal opening 61 to allow the needle 30 to pass therethrough; a second jaw member 70 mounted to the distal end 13 of the shaft 12 and integral to the distal end of the shaft, the second jaw member 70 comprising a through opening/window 75 and a securing mechanism 77 to secure a flexible strand 80 at its most distal end, the securing mechanism 77 being located in about same plane as the through opening/window 75; and a handle assembly 40 configured to move the needle 30 from the first jaw member 60 to the second jaw member 70. The flexible strand 80 includes a tail 81 and a loop. The loop can terminate in the tail. The loop can be a flexible, continuous, uninterrupted loop. The loop can be a knotted loop. The tail 81 is secured to the first jaw member 60. The loop 85 can be secured to handle assembly 40. The loop 85 can be secured to a ring 88 of the handle assembly 40. The ring 88 is configured to be removed from the handle assembly and to slide over the distal tip 50 of the suture passer 100, to allow the tail 81 to pass through loop 85 and to form, therefore, a suture stitch 89 around and through the tissue 90 (or tissue 90 and graft 91) and at repair site 101, 102.

According to an exemplary and illustrative embodiment only, a method of suturing tissue comprises: (i) loading a suture 80 formed of a suture loop 85 and a tail 81 onto instrument 100; (ii) piercing tissue 90 (or graft 91 and tissue 90) with a tip of the instrument 100 and at two different locations A, B within the tissue 90 (or graft 91 and tissue 90); (iii) advancing tail 81 through the tissue 90 (or graft 91 and tissue 90) from location A to location B and from a lower jaw 60 to an upper jaw 70 of the instrument 100; (iv) pulling the instrument 100 out of the tissue 90 (or graft 91 and tissue 90) to allow tail 81 to be secured in a securing mechanism 77 at a most distal end of the upper jaw 70 of instrument 100; and (v) passing the tail 81 through suture loop 85 to form a cinch 89 around and through the tissue 90 (or graft 91 and tissue 90) (a direct pass cinch stitch or mattress stitch) of repair 101, 102. In an embodiment, repair 101, 102 is a knotless repair. In an embodiment, repair 101, 102 is a knotted repair.

Flexible strand 80 can be coated (partially or totally) with wax (beeswax, petroleum wax, polyethylene wax, or others), silicone (Dow Corning silicone fluid 202A or others), silicone rubbers (Nusil Med 2245, Nusil Med 2174 with a bonding catalyst, or others) PTFE (Teflon, Hostaflon, or others), PBA (polybutylate acid), ethyl cellulose (Filodel) or other coatings, to improve lubricity of the suture, loop security, pliability, handleability or abrasion resistance, for example. Flexible strand 80 can be also provided with tinted tracing strands, or otherwise contrast visually with other areas/regions of the construct, which remains a plain, solid color, or displays a different tracing pattern, for example. Various structural elements of flexible strand 80 such as loop 85 and/or tail 81 may be visually coded, making identification and handling of the suture loops and ends simpler. Easy identification of suture in situ is advantageous in surgical procedures.

The term "high strength suture" is defined as any elongated flexible member, the choice of material and size being dependent upon the particular application. For the purposes of illustration and without limitation, the term "suture" as used herein may be a cable, filament, thread, wire, fabric, or any other flexible member suitable for tissue fixation in the body.

What is claimed is:

1. A suture passer comprising:

a shaft having a longitudinal axis, a distal end and a proximal end;

a first jaw member integral to the distal end of the shaft, the first jaw member having a passage for receiving a needle and a distal opening to allow the needle to pass therethrough;

a second jaw member mounted to the distal end of the shaft and integral to the distal end of the shaft, the second jaw member comprising a through opening and a securing mechanism, wherein the securing mechanism is configured to catch a flexible strand at a most distal end of the second jaw member when the suture passer is pulled out of tissue, or tissue and associated graft, the securing mechanism and the through opening being located in about a same plane parallel to the longitudinal axis of the shaft, wherein each of the first jaw member and the second jaw member terminates in a sharp tip configured to pierce the tissue, or the tissue and the associated graft, wherein the flexible strand runs outside the shaft and along the shaft in a direction about parallel to the longitudinal axis of the shaft, and is positioned within the distal opening of the first jaw to rest about perpendicular to the longitudinal axis of the shaft; and a handle assembly configured to move the needle from the first jaw member to the second jaw member.

2. The suture passer of claim 1, wherein the first jaw member has a first length and the second jaw member has a second length, and wherein the first length is different from the second length.

3. The suture passer of claim 2, wherein the first length is smaller than the second length.

4. The suture passer of claim 1, wherein the flexible strand comprises a loop terminating in a tail, and wherein the loop is secured to the handle assembly and the tail is secured to the first jaw member.

5. The suture passer of claim 4, wherein the loop is a continuous, flexible loop secured to a ring of the handle assembly, wherein the ring is configured to detach from the suture passer and slide over the distal end of the suture passer and over the tail.

6. The suture passer of claim 4, wherein the loop is a pre-formed cerclage loop or a Weston loop.

7. The suture passer of claim 1, wherein the securing mechanism of the second jaw member is a suture catch spike that secures the flexible strand to the second jaw member when the suture passer is pulled out of tissue, or out of tissue and associated graft.

8. The suture passer of claim 1, wherein the flexible strand is suture.

* * * * *